(12) United States Patent
Griffin

(10) Patent No.: US 9,116,539 B1
(45) Date of Patent: Aug. 25, 2015

(54) ELECTROLARYNX THUMBWHEEL ARRANGEMENT

(71) Applicant: Clifford Jay Griffin, Murrieta, CA (US)

(72) Inventor: Clifford Jay Griffin, Murrieta, CA (US)

( * ) Notice: Subject to any disclaimer, the term of this patent is extended or adjusted under 35 U.S.C. 154(b) by 294 days.

(21) Appl. No.: 13/918,946

(22) Filed: Jun. 15, 2013

Related U.S. Application Data

(60) Provisional application No. 61/749,446, filed on Jan. 7, 2013.

(51) Int. Cl.
*G05G 1/10* (2006.01)

(52) U.S. Cl.
CPC ........................................ *G05G 1/10* (2013.01)

(58) Field of Classification Search
USPC ............................................................ 381/70
See application file for complete search history.

(56) References Cited

U.S. PATENT DOCUMENTS

| | | | | |
|---|---|---|---|---|
| 3,978,286 A | * | 8/1976 | Watson | 381/70 |
| 5,812,681 A | * | 9/1998 | Griffin | 381/70 |
| 6,252,966 B1 | * | 6/2001 | Griffin | 381/70 |
| 2003/0031324 A1 | * | 2/2003 | Lukacovic | 381/70 |
| 2003/0031325 A1 | * | 2/2003 | Lukacovic | 381/70 |
| 2003/0031326 A1 | * | 2/2003 | Lukacovic | 381/70 |
| 2013/0294613 A1 | * | 11/2013 | Nagel et al. | 381/70 |

* cited by examiner

*Primary Examiner* — Brenda Bernardi
(74) *Attorney, Agent, or Firm* — Loyal McKinley Hanson

(57) ABSTRACT

An electrolarynx includes a case and a thumbwheel component within its hollow interior that includes a wheel with a peripheral edge. A wheel-receiving slot extends from the exterior surface of the case to the hollow interior, and the wheel is disposed partially within that slot so that the peripheral edge of the wheel is accessible with a finger of a user from the exterior of the case for purposes of engaging and turning the wheel. The case includes a radially outward protruding wheel-protecting structure next to the wheel-receiving slot that shields (i.e., protects) the wheel from an impact directed parallel to the rotational axis of the wheel, without the radially outward protruding wheel-protecting structure preventing the user from engaging and turning the wheel with a finger of the user.

5 Claims, 7 Drawing Sheets

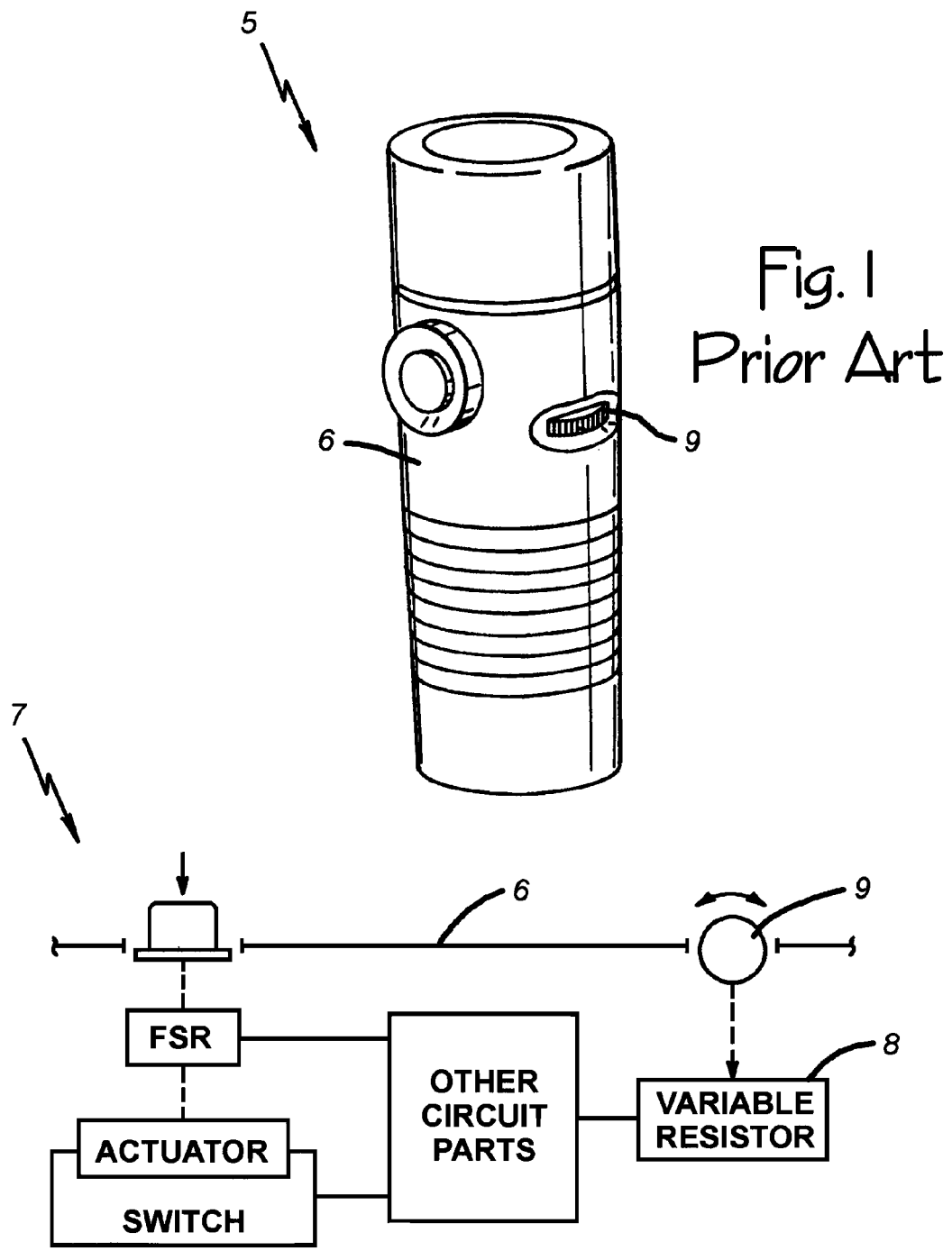

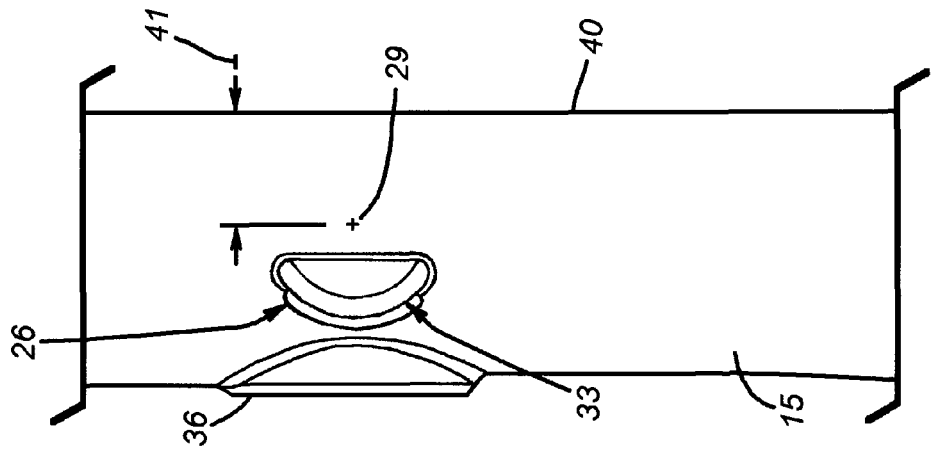
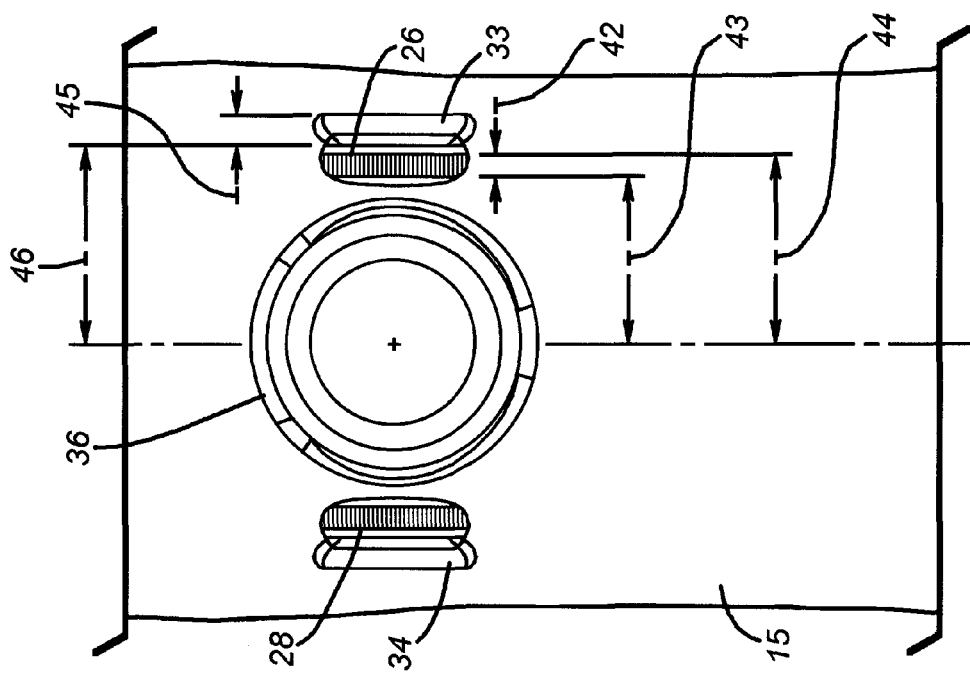

ELECTROLARYNX THUMBWHEEL ARRANGEMENT

CROSS REFERENCE TO RELATED APPLICATION

This application claims the benefit of U.S. Provisional Patent Application Ser. No. 61/749,446 filed Jan. 7, 2013.

BACKGROUND OF THE INVENTION

1. Technical Field

This invention relates generally to electromechanical speech aids commonly referred to as artificial larynxes and electrolarynxes, and more particularly to an electrolarynx thumbwheel arrangement that helps avoid early thumbwheel component failure.

2. Description of Related Art

Persons without normal use of their vocal cords or larynx often speak with the aid of a prosthetic device called an "electrolarynx." A typical existing electrolarynx includes a battery-powered electromechanical transducer within a four-inch to five-inch long, cylindrically shaped, electrolarynx case. The transducer vibrates a diaphragm at one end of the case to produce an electrolarynx tone having a fundamental frequency in the speech range of the average human voice.

To speak, the user introduces this artificially generated electrolarynx tone into a resonant speech cavity (i.e., the mouth, nose, or pharynx) by placing the diaphragm end of the electrolarynx case near the resonant speech cavity. The user grasps the case, actuates the ON-OFF switch and the VOLUME control, and then presses the diaphragm end against the outside of their throat so that vibrations travel through the throat tissues and into the mouth and throat. While introducing the electrolarynx tone that way, the user modulates the tone by varying the shape of the resonant speech cavity and by making the usual tongue, teeth, and lip constrictions so as to articulate the modulated tone as human speech.

The VOLUME control of an electrolarynx (or other control circuitry of the electrolarynx) often includes a user-accessible electronic control component called a thumbwheel potentiometer or thumbwheel variable resistor (i.e., a "thumbwheel component"). The thumbwheel component is located in the electrolarynx interior. It includes a wheel that a user turns for purposes of controlling volume, pitch, or some other aspect of the electrolarynx. The wheel has a partially exposed edge extending through a slot in the electrolarynx case in such a way that the user can engage the edge of the wheel from the exterior of the electrolarynx. The user turns the wheel with their thumb or other finger in order to thereby control the volume or other electrolarynx function. The exposed edge of the wheel is as usually knurled to aid the user in that effort.

One concern common to manufacturers, distributors, retailers, and users of such electrolarynxes is early failure of the thumbwheel component. It seems that thumbwheel components as described above often have a much shorter life span than anticipated. They malfunction in one way or another much sooner than desired, with electrolarynx downtime resulting, together with the time and expense of repair and/or replacement, and so a need exits for a way to alleviate that concern.

SUMMARY OF THE INVENTION

In view of the foregoing, it is a primary object of the present invention to provide an electrolarynx that alleviates the concern outlined above. The present invention achieves this objective predicated on the inventor's realization that the exposed wheels of the thumbwheel components on some existing electrolarynxes are vulnerable to impact during use, and that such impact (i.e., the action of some object coming forcibly into contact with the exposed wheel) can result in early thumbwheel component failure (e.g., when the electrolarynx is dropped or otherwise mishandled). Based upon that realization, the present invention alleviates the concern outlined above by providing an electrolarynx having a protruding thumbwheel guard on the electrolarynx case next to the partially exposed wheel. That arrangement shields and protects the partially exposed wheel from harmful impact while still allowing user access to its knurled edge.

To paraphrase some of the more precise language appearing in the claims and further introduce the nomenclature used, an electrolarynx constructed according to the invention includes a case and at least one thumbwheel component (i.e., a first thumbwheel component). The case extends along a central axis of elongation of the case and it defines a hollow interior of the case. The first thumbwheel component is mounted within the hollow interior and it includes a first wheel with a first peripheral edge centered on a rotational axis of the first wheel. The first peripheral edge of the first wheel is disposed partially within a first slot in the case (i.e., a first wheel-receiving slot that extends from the exterior surface to the hollow interior) so that the first peripheral edge of the first wheel is accessible by a user from the exterior of the case for purposes of engaging and turning the first wheel.

According to the major aspect of the invention, the case includes a first wheel-protecting structure next to the first wheel-receiving slot. The wheel-protecting structure protrudes radially outward from the rest of the case in order to serve the function of shielding and thereby protecting the first wheel from an impact directed parallel to the rotational axis of the first wheel. It does so without preventing the user from engaging and turning the first wheel with a finger of the user.

Preferably, the first radially outward protruding wheel-protecting structure is integrally molded with the slot-defining portion of the case (e.g., a first section or half of the case that is discussed later on). In addition, one embodiment includes a second thumbwheel component (e.g., a PITCH control) having a second wheel that is at least partially disposed within a second wheel-receiving slot defined by the electrolarynx case. The second thumbwheel component is accompanied by a second radially outward protruding wheel-protecting structure next to the second slot.

Thus, the invention alleviates the concern outlined above by shielding and thereby protecting the partially exposed wheel of the thumbwheel component from harmful impact while still allowing user access to the exposed periphery. The following illustrative drawings and detailed description make the foregoing and other objects, features, and advantages of the invention more apparent.

BRIEF DESCRIPTION OF THE DRAWINGS

FIG. 1 of the drawings is a perspective view of an existing electrolarynx constructed according to the prior art;

FIG. 2 of the drawings is a block circuit diagram of components of the existing electrolarynx;

FIG. 8 is an enlarged front view of a portion of the front section of the case, showing details of relative size and component placement for the illustrated embodiment; and FIG. 9 is an enlarged side view of a portion of the front section of the case showing additional details of size and component placement.

DESCRIPTION OF THE PREFERRED EMBODIMENTS

Figure 3:
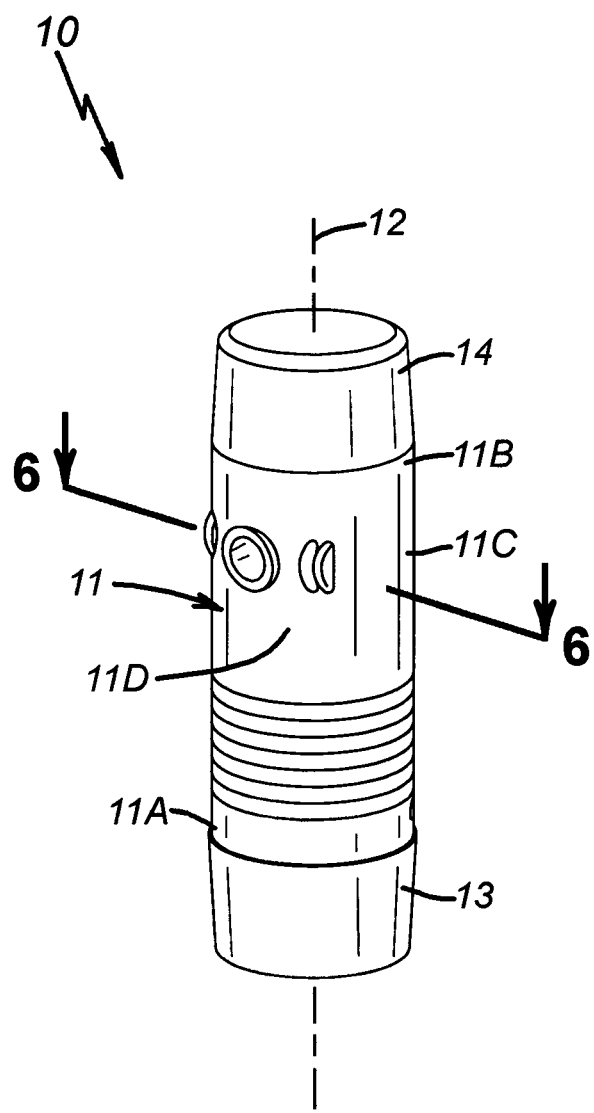
FIG. 3 is a perspective view of a thumbwheel-guarded electrolarynx constructed according to the present invention.

FIG. 1 of the drawings shows an electrolarynx 5 constructed according to the prior art. It includes an electrolarynx case 6 that houses electronic circuitry 7 shown in block diagram form in FIG. 2. The electronic circuitry 7 includes a pushbutton for actuating a force-sensitive resistor (FSR) and an ON-OFF switch via a switch actuator component, to thereby control other circuit parts. The electronic circuitry 7 also includes a thumbwheel component 8 having a wheel 9 with a partially exposed edge that extends partially through a slot in the case 6 in such a way that the user of the electrolarynx 5 can turn the wheel 9 with a finger for volume-control purposes. It is the thumbwheel component 8 with its wheel 9 that is prone to failure.

Now consider FIGS. 3 through 8. They show various details of an electrolarynx 10 constructed according to the present invention. Generally, the electrolarynx 10 includes a case 11 that extends along a central axis of elongation 12 of the case 11, between a first or bottom end cap 13 at a rearward end 11A of the case and a second or top end cap 14 at a forward end 11B of the case. The user grasps the case 11, presses the top end cap 14 (i.e., the sound-producing transducer portion at the forward end of the electrolarynx 10) against the outside of their throat in order to introduce the electrolarynx tone to their mouth and throat, and then modulates that tone by varying the shape of the resonant speech cavity and by making the usual tongue, teeth, and lip constrictions so as to articulate the modulated tone as human speech.

Figure 4:
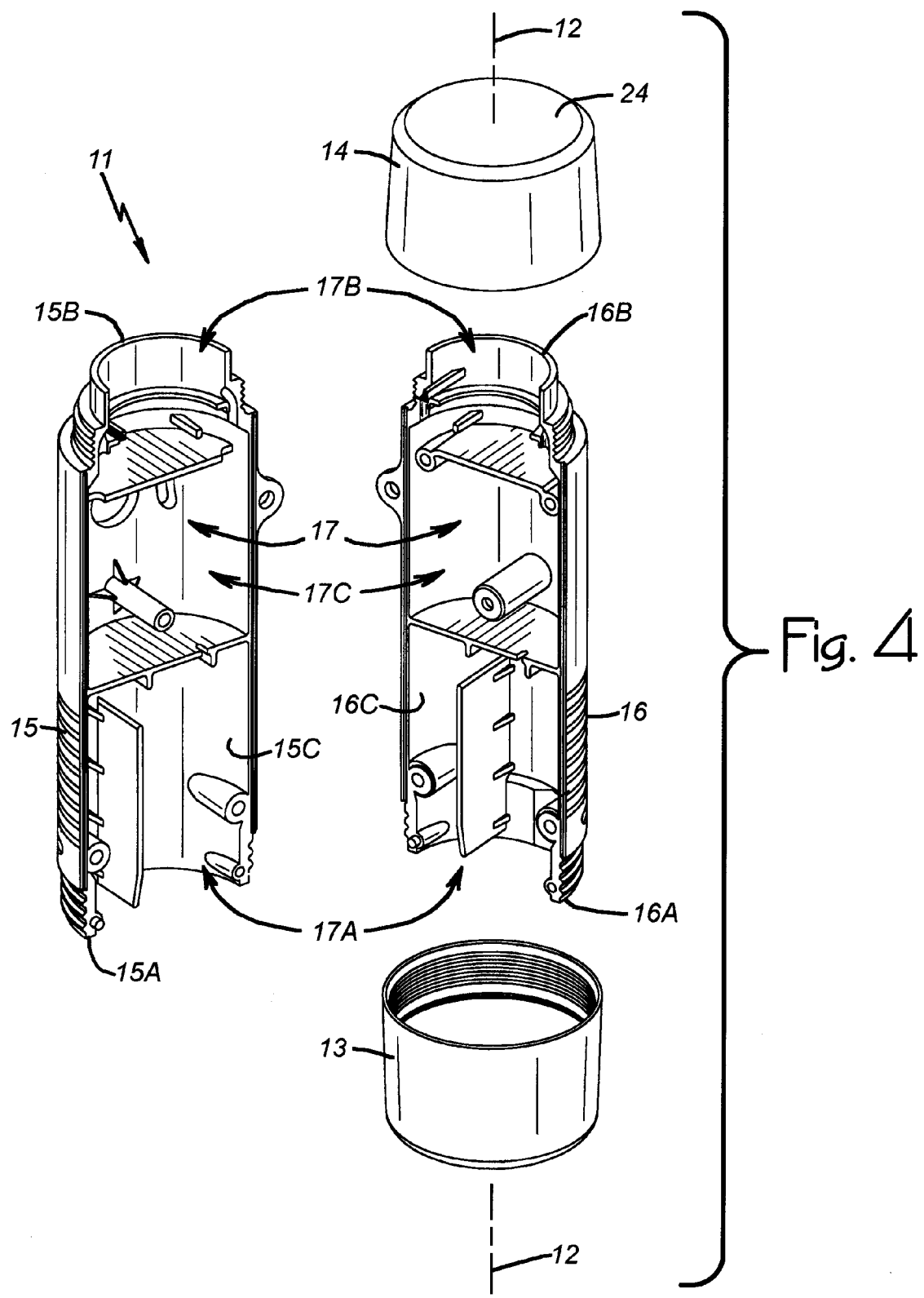
FIG. 4 is an exploded view of the thumbwheel-guarded electrolarynx case and its two end caps.

FIG. 4 is an exploded view of the electrolarynx 10 that shows further details of the case 11. The case 11 is a handheld molded-plastic component having an overall length of about 4.6 inches measured along the central axis of elongation 12. Of course, that dimension provides an idea of the size of the various components of the illustrated embodiment; it is not critical to the present invention. The case 11 includes a first section or half 15 and a second section or half 16 that, when fully assembled, are held together by the bottom and top end caps 13 and 14. The assembler person screws the bottom and top end caps 13 and 14 onto the first and second sections 15 and 16, in threaded engagement of the first and second sections 15 and 16.

The first half 15 of the case 11 has a bottom end 15A, a top end 15B and an inner wall 15C extending between the bottom and top ends 15A and 15B. Similarly, the second half 16 has a bottom end 16A, a top end 16B, and an inner wall 16C extending between the bottom and top ends 16A and 16B. When the first and second halves 15 and 16 are fully assembled, the inner walls 15C and 16C of the first and second halves 15 and 16 combine as an inner wall 15C-16C (i.e., the combination of 15C and 16C) that defines a hollow interior 17 of the case 11, a hollow interior that is centered on the central axis of elongation 12 that houses various electronic components of the electrolarynx 10. With the first and second sections 15 and 16 fully assembled, the case 11 and the hollow interior 17 extend along the central axis of elongation 12 of the case 11, from a proximal end portion 17A of the hollow interior 17 (or rearward end portion) at the rearward end 11A of the case 11 (identified in FIG. 3) to a distal end portion 17B of the hollow interior 17 (or forward end portion) at a forward end 11B of the case 11 (identified in FIG. 3), and it includes a mid portion 17C (FIGS. 4 and 5) that provides a space for a circuit board.

Figure 5:
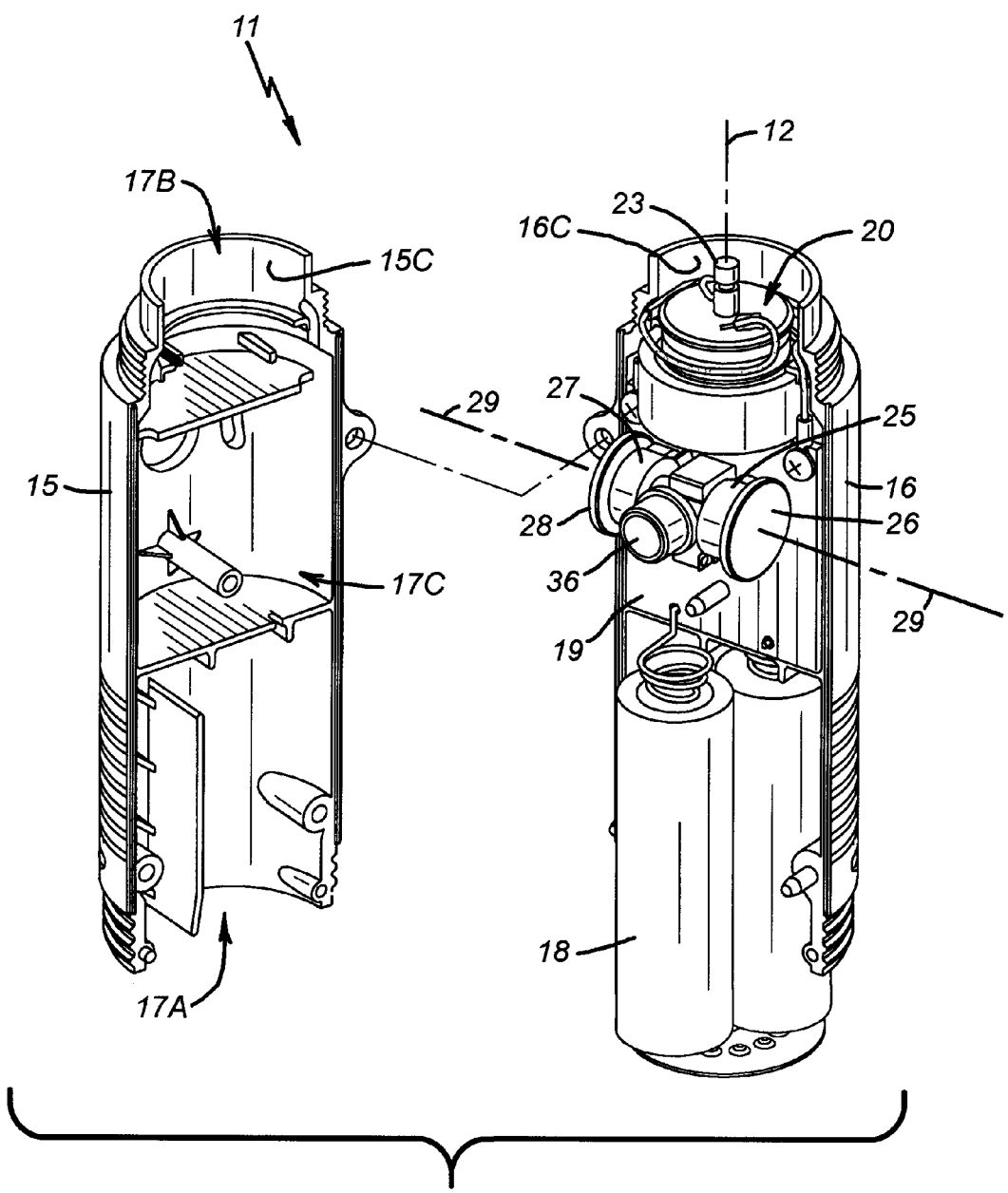
FIG. 5 is an exploded view of the thumbwheel-guarded electrolarynx case after electronic components have been assembled within the case.

Some electronic components of the electrolarynx 10 have been added to the second half 16 of the case 11 in the exploded view of FIG. 5, including a battery power supply 18 in the proximal end portion 17A of the hollow interior 17, a circuit board 19 in the mid portion 17C, and a transducer component 20 in the distal end portion 17B. The transducer component 20, also referred to as an electro-mechanical transducer assembly, is a known type of component that includes a coil of magnet wire for producing a magnetic field that causes a plunger 23 aligned with the central axis of elongation 12 to vibrate against a button-like diaphragm 24 (FIG. 4), thereby to produce a buzzing electrolarynx sound.

Figure 6:
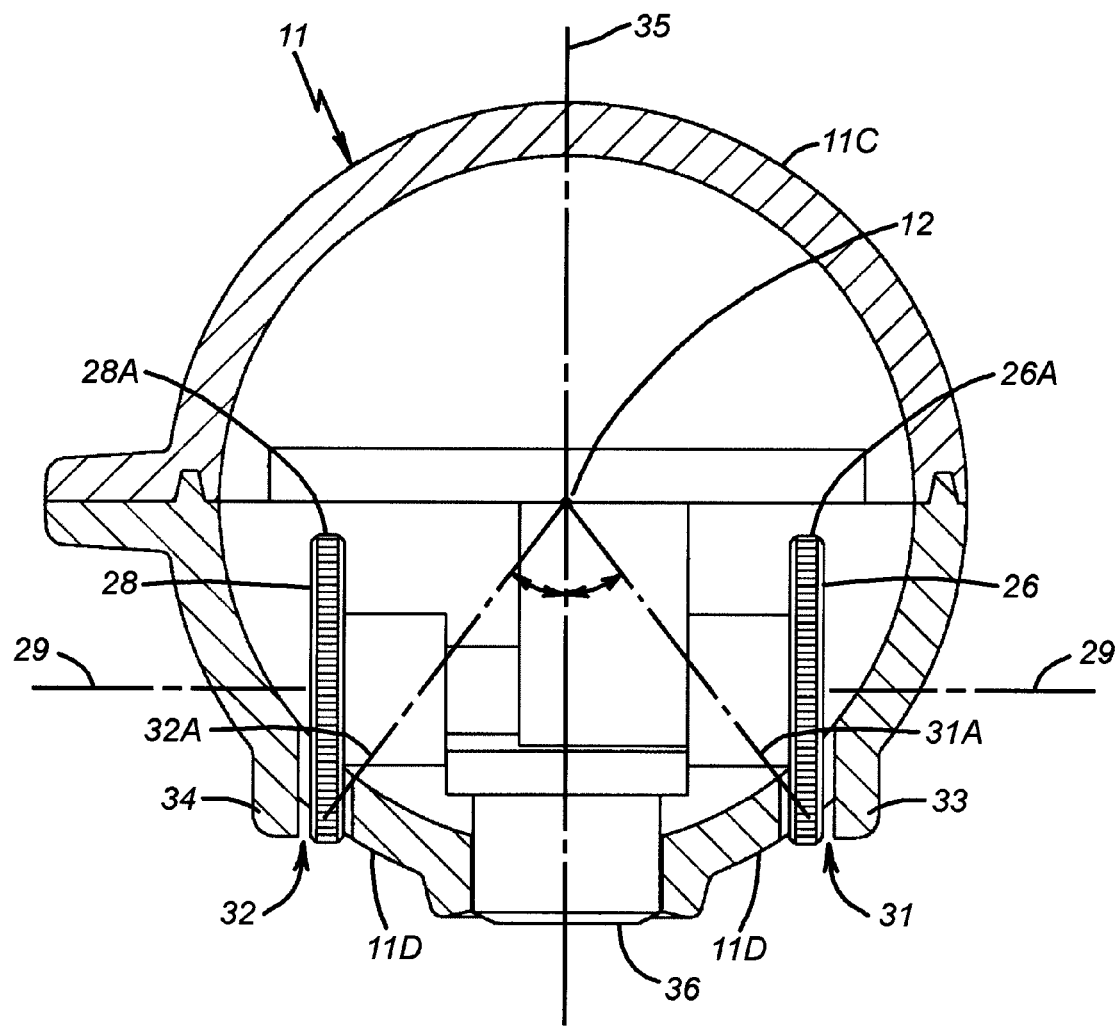
FIG. 6 is an enlarged cross section of the fully assembled electrolarynx, as viewed in a plane perpendicular to the central axis of elongation of the electrolarynx that contains a section line 6-6 in FIG. 3.
Figure 7:
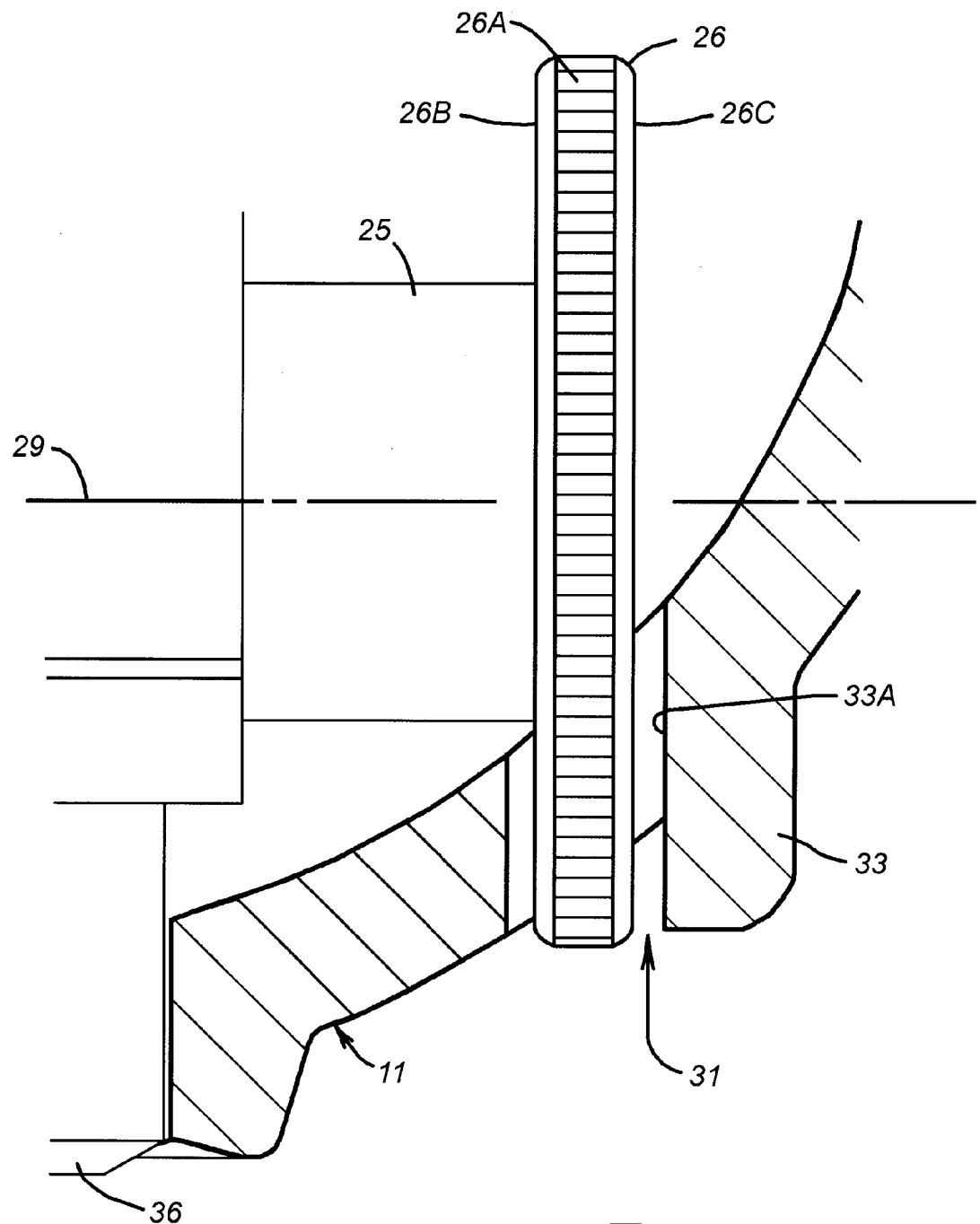
FIG. 7 is a further enlarged cross section of similar to FIG. 6, showing just the first thumbwheel arrangement.

A first thumbwheel component 25, having a user-accessible first wheel 26, is mounted on the circuit board 19, within the hollow interior of the case 11, in alignment with a second thumbwheel component 27 having a user-accessible second wheel 28. The first and second wheels 26 and 28 are rotatable about a common thumbwheel rotational axis 29 (FIGS. 5, 6, and 7) and they extend partially through openings 31 and 32 in the case 11 (i.e., first and second wheel-receiving slots) so that the user can access them (i.e., rotate them). The openings 31 and 32 extend from an exterior surface 11C of the case 11 (FIGS. 3 and 6) to the hollow interior 17 of the case 11 (FIG. 4), being so defined by an opening-defining portion 11D of the case 11 (FIGS. 3 and 6). The first and second wheels 26 and 28 are disposed partially within the first and second wheel-receiving slots 31 and 32 so that first and second peripheral edges 26A and 28A of the first and second wheels 26 and 28 are accessible by a user with a finger of the user for purposes of engaging and turning the wheels. The user turns (i.e., rotates) the first wheel 26 of the first thumbwheel component 25 to adjust the volume of the buzzing electrolarynx sound. The user turns the second wheel 28 of the second thumbwheel component 27 to adjust the pitch (also sometimes called the tone).

According to the major aspect of the invention, protruding first and second wheel-protecting structures 33 and 34 (FIGS. 6 and 7) are provided to protect the first and second wheels 26 and 28 from damaging impact. They are located next to the openings 31 and 32, and thereby next to exposed portions of the peripheral edges 26A and 28A of the wheels 26 and 28 (i.e., those portions of the peripheral edges that are extending through the openings 31 and 32) So located, the wheel-protecting structures 33 and 34 protect the exposed portions of the peripheral edges 26A and 28A of the wheels 26 and 28 from an impacting force component directed toward the exposed portions in a direction parallel to the common thumbwheel rotational axis 29. In other words, the case 11 includes first and second radially outward protruding wheel-protecting structures 33 and 34 next to the first and second wheel-receiving slots 31 and 32 that serve the function of protecting the first and second wheels 26 and 28 from an impact directed parallel to the rotational axis 29 of the first and second wheels, without the radially outward protruding wheel-protecting structures 33 and 34 preventing the user from engaging and turning the first and second wheels with a finger of the user.

More specifically, the common thumbwheel rotational axis 29 of the wheels 26 and 28 is perpendicular to a reference plane 35 that contains the central axis of elongation 12 of the case 11, as shown in FIG. 6. In addition, the wheel-receiving slots 31 and 32 are located on respective ones of a first reference radius 31A and a second reference radius 32A (FIG. 6), with the radii 31A and 32A being located at an angular distance from the reference plane 35 that lies in a range of about twenty degrees to about sixty degrees, depending on the precise details of any particular implementation of the present invention. The illustrated radii (indicated by the double-headed arrows in FIG. 6) are, for example, at about thirty-five to forty degrees from the reference plane 35. Of course, other component orientations fall within the broader scope of the invention, although having the wheels and related structure disposed as illustrated is preferred for the illustrated two-thumbwheel electrolarynx case 11. So arranged, the wheel-receiving slot 31 is located in a protected position intermediate the first wheel-protecting structure 33 and a pushbutton structure 36, while the second wheel-receiving slot 32 is located in a protected position intermediate the second wheel-protecting structure 34 and the pushbutton structure 36.

As a further idea of size and component placement for the illustrated embodiment of the present invention, the wheel 26 of the thumbwheel component 25 measures about 0.530 inches in diameter (a radius of 0.265 inches), while the wheel-receiving slot 31 for it in the case 11 measures about three thirty-seconds of an inch wide and about eleven thirty-seconds of an inch long. The wheel-protecting structures 33 and 34 are somewhat circularly shaped (e.g., centered on the rotational axis 29 of the wheels 26 and 28) so that they follow the profile of the exposed peripheral edges 26A and 28A of the first and second wheels 26 and 28 in order to better shield the wheels from impact. The peripheries of the wheel-protecting structures extend along arcs that are centered on the rotational axis 29, and those arcs follow the profile of the exposed peripheral edges 26A and 28A as illustrated, having radii that are slightly less than that of the wheels 26 and 28 in order to achieve a desired ease of user access to the wheels for wheel-turning purposes (e.g., about 0.230 inches for the wheel-protecting structure 33 and slightly larger for the wheel-protecting structure 34 in order to avoid unintended adjustments of the wheel that adjusts PITCH).

FIGS. 8 and 9 show additional size information. The rotational axis 29 is located a distance of about 0.276 inches, from a line 40 in FIG. 9 that represents the joint between the first and second case sections 15 and 16. A reference numeral 41 in FIG. 9 identifies that dimension (the case sections 14 and 15 were mentioned earlier with reference to FIGS. 4 and 5). The width of the wheel 26 is about 0.055 inches (a dimension 42 in FIG. 8), with an inward side of the wheel 26 being spaced about 0.406 inches from the reference plane 35 (a dimension 43) and an outward side of the wheel 26 being spaced about 0.461 inches from the reference plane 35. The width of the wheel-protecting structure 33 is about 0.075 inches (a dimension 45 in FIG. 8) with a wheel-facing inward side spaced about 0.484 inches from the reference plane 35 (a dimension 46). An inward side 26B of the wheel 26 and an outward side 26C of the wheel 26 are identified in FIG. 7, along with a wheel-facing inward side 33A of the wheel-protecting structure 33. The corresponding size, shape, and orientation of the wheel 28 is similar. Of course, the foregoing dimensioning provides an example. Other dimensioning may be applied within the inventive concepts expressed for the present invention.

Thus, the invention shields and protects the partially exposed wheel of an electrolarynx thumbwheel component from harmful impact while still allowing user access to the exposed periphery. The curvature of the case provides protection on the inward side of the wheel while the protrusion provides protection on the outward side. Although an exemplary embodiment has been shown and described, one of ordinary skill in the art may make many changes, modifications, and substitutions without necessarily departing from the spirit and scope of the invention. As for the specific terminology used to describe the exemplary embodiment, it is not intended to limit the invention; each specific term is intended to include all technical equivalents that operate in a similar manner to accomplish a similar purpose or function. The technique of "shielding" and "protecting" the exposed peripheral edges include at least partially shielding and at least partially protecting them.

What is claimed is:

1. An electrolarynx, comprising:
   a case extending along a central axis of elongation of the case, said case defining a hollow interior of the case; and
   a first thumbwheel component mounted within the hollow interior of the case, said first thumbwheel component having a first wheel with a first peripheral edge centered on a rotational axis of the first wheel;
   wherein the case defines a first wheel-receiving slot in the case that extends from the exterior surface of the case to the hollow interior of the case;
   wherein the first wheel is disposed partially within the first slot so that the first peripheral edge of the first wheel is accessible by a user with a finger of the user for purposes of engaging and turning the first wheel; and
   wherein the case includes a first radially outward protruding wheel-protecting structure next to the first wheel-receiving slot that serves the function of protecting the first wheel from an impact directed parallel to the rotational axis of the first wheel, without said first radially outward protruding wheel-protecting structure preventing the user from engaging and turning the first wheel with a finger of the user.

2. An electrolarynx as recited in claim 1, wherein the first radially outward protruding wheel-protecting structure is integrally molded with a slot-defining portion of the case.

3. An electrolarynx as recited in claim 1, further comprising:
   a second thumbwheel component with a second wheel that is at least partially disposed within a second wheel-receiving slot defined by the case of the electrolarynx; and
   a second radially outward protruding wheel-protecting structure next to the second slot.

4. An electrolarynx as recited in claim 1, wherein:
   the case of the electrolarynx includes a radially outward protruding pushbutton that is spaced apart circumferentially from the first radially outward protruding wheel-protecting structure no more than sixty degrees; and
   the first slot is disposed intermediate the radially outward protruding pushbutton and the first radially outward protruding wheel-protecting structure.

5. An electrolarynx as recited in claim 4, further comprising:
   a second thumbwheel component with a second wheel that is at least partially disposed within a second wheel-receiving slot defined by the case of the electrolarynx such that the radially outward protruding pushbutton is disposed intermediate the first and second wheel-receiving slots; and
   a second radially outward protruding wheel-protecting structure next to the second slot.

* * * * *